US008044027B2

(12) United States Patent
Dal Farra et al.

(10) Patent No.: US 8,044,027 B2
(45) Date of Patent: *Oct. 25, 2011

(54) UTILIZATION OF PEPTIDES AS ACTIVE INGREDIENTS FOR SLIMMING

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 180 days.

This patent is subject to a terminal disclaimer.

(21) Appl. No.: 12/300,597

(22) PCT Filed: May 11, 2007

(86) PCT No.: PCT/FR2007/000803
§ 371 (c)(1),
(2), (4) Date: Nov. 12, 2008

(87) PCT Pub. No.: WO2007/135268
PCT Pub. Date: Nov. 29, 2007

(65) Prior Publication Data
US 2009/0264372 A1    Oct. 22, 2009

(30) Foreign Application Priority Data
May 12, 2006   (FR) ...................... 06 04251

(51) Int. Cl.
A61K 38/00 (2006.01)
A61K 38/08 (2006.01)
A61Q 19/00 (2006.01)
A61Q 19/06 (2006.01)
C07K 7/00 (2006.01)
C07K 7/06 (2006.01)

(52) U.S. Cl. ....... 514/18.6; 514/1.1; 514/21.7; 530/300; 530/329

(58) Field of Classification Search ...................... None
See application file for complete search history.

(56) References Cited

U.S. PATENT DOCUMENTS

| 4,966,848 | A | * | 10/1990 | Smith et al. | .................. | 435/193 |
| 5,223,421 | A | * | 6/1993 | Smith et al. | .................. | 435/193 |
| 5,837,218 | A | * | 11/1998 | Peers et al. | .................. | 424/1.69 |
| 2003/0064411 | A1 | * | 4/2003 | Herath et al. | .................. | 435/7.2 |

FOREIGN PATENT DOCUMENTS

| FR | 2858769 | 2/2005 |
| WO | 2005002527 | 1/2005 |

OTHER PUBLICATIONS

Definition of derivative from http://cancerweb.ncl.ac.uk/omd/about.html, pp. 1-5. Accessed Jul. 7, 2005.*
SIRT sequence from GenBank Accession No. NP_036372, p. 1. Accessed Dec. 30, 2010.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Porcu M et al., "The emerging therapeutic potential of sirtuin-interacting drugs: from cell death to lifespan extension", Trends in Pharmacological Sciences, Elsevier, Haywarth, GB, vol. 26, No. 2, Feb. 2005, pp. 94-103, XP004727629.
International search report in corresponding PCT/FR2007/000803, Feb. 13, 2008.

* cited by examiner

*Primary Examiner* — Julie Ha
(74) *Attorney, Agent, or Firm* — Young & Thompson

(57) ABSTRACT

A method of using proteins of the SIRT family or of polypeptide or peptide fragments of SIRT proteins as an active ingredient for slimming, alone or in combination with at least one other active agent, in a cosmetic composition or for the preparation of a pharmaceutical and/or dermatological composition. The invention also includes the use of the peptides for treatment of cellulite and/or used to decrease, eliminate or prevent excess fat beneath the skin.

16 Claims, No Drawings

SEQUENCE LISTING

<160> NUMBER OF SEQ ID NOS: 6

<210> SEQ ID NO 1
<211> LENGTH: 6
<212> TYPE: PRT
<213> ORGANISM: Artificial
<220> FEATURE:
<223> OTHER INFORMATION: synthetic peptide

<400> SEQUENCE: 1

Gly Ala Gly Ile Ser Thr
1               5

<210> SEQ ID NO 2
<211> LENGTH: 8
<212> TYPE: PRT
<213> ORGANISM: Artificial
<220> FEATURE:
<223> OTHER INFORMATION: synthetic peptide

<400> SEQUENCE: 2

Gly Ile Pro Asp Phe Arg Ser Pro
1               5

<210> SEQ ID NO 3
<211> LENGTH: 6
<212> TYPE: PRT
<213> ORGANISM: Artificial
<220> FEATURE:
<223> OTHER INFORMATION: synthetic peptide

<400> SEQUENCE: 3

Gly Ile Pro Asp Phe Arg
1               5

<210> SEQ ID NO 4
<211> LENGTH: 7
<212> TYPE: PRT
<213> ORGANISM: Artificial
<220> FEATURE:
<223> OTHER INFORMATION: synthetic peptide

<400> SEQUENCE: 4

Gly Ile Pro Asp Phe Arg Ser
1               5

<210> SEQ ID NO 5
<211> LENGTH: 7
<212> TYPE: PRT
<213> ORGANISM: Artificial
<220> FEATURE:
<223> OTHER INFORMATION: synthetic peptide

<400> SEQUENCE: 5

Gly Leu Tyr Asp Asn Leu Glu
1               5

<210> SEQ ID NO 6
<211> LENGTH: 7
<212> TYPE: PRT
<213> ORGANISM: Artificial
<220> FEATURE:
<223> OTHER INFORMATION: synthetic peptide

```
<400> SEQUENCE: 6

Thr Gln Asn Ile Asp Thr Leu
1               5
```

UTILIZATION OF PEPTIDES AS ACTIVE INGREDIENTS FOR SLIMMING

The invention concerns the field of cosmetics and pharmaceuticals, in particular, the field of dermatology.

The purpose of the present invention is the utilization of proteins of the SIRT family or polypeptide or peptide fragments of SIRT proteins as an active ingredient for slimming, alone or in combination with at least one other active agent, in a cosmetic composition or for the preparation of a pharmaceutical and/or dermatological composition. Said peptides are intended, in particular, for treatment of cellulite and/or used to decrease, eliminate or prevent excess fat beneath the skin.

The study of the SIRT genes and the corresponding proteins has provided new therapeutic targets allowing for an intervention in the regulation of the energy metabolism of mammals. The SIRT proteins are part of the family of sirtuins, which are NAD+ dependent nuclear proteins responsible for deacetylation of histones (Rine J. et Al, *Genetics,* 1979). Several studies in organisms as diverse as *C. Elegans* or mammals have shown that there is a relation between energy input and life span and that the SIRT protein was responsible for this linkage. Thus, a reduction in calorie intake increases the life span of yeast (Tissenbaum et Al, *Nature,* 2001). Furthermore, recent studies have shown that SIRT1 causes mobilization of fat in the adipocytes (Picard F. et al, *Nature,* 2004). The SIRT proteins are currently considered to be potential therapeutic targets for treatment of dysfunctions or ailments connected with obesity, diabetes, or even hyperlipidemia, among others (WO 03/061681, US 2005/0164969).

The skin is the integument covering the entire surface of the body, made up of three distinct superimposed compartments: the epidermis (outer epithelium), the dermis (conjunctive tissue for support) and the hypodermis. The epidermis is a stratified epithelium constituting the external structure of the skin and providing its protective function. The dermis is a support tissue involved in the strength, the elasticity, and especially the tonicity of the skin and/or mucous membranes. Beneath the dermis is a layer of adipose tissues: the hypodermis.

The hypodermis is made up of a layer of white adipose tissue organized into lobules attached to the lower part of the dermis by rows of collagen fibers and elastic fibers. It is made up of large vacuolized cells, the adipocytes, almost entirely filled with triglycerides. These cells can rapidly change in volume as one loses or gains weight, and can measure from 40 to 120 μm in diameter, corresponding to a variation of 27 times in volume.

The hypodermal adipose tissue is the largest energy reservoir of the body. It is able to store lipids in the form of triglycerides by a process of lipogenesis, and then release them in the form of fatty acids and glycerol by a process of lipolysis. It is the equilibrium between these two metabolic pathways which governs adiposity. The lipid reserves of the body are constantly being renewed and have a close relation to the nutritional intake and energy needs of the body.

If a disequilibrium occurs in the body between the processes of lipogenesis and lipolysis, the volume and the number of adipocytes may increase; one speaks of adipocyte hypertrophy and hyperplasia. Excessive development of the adipose mass may then translate into modifications in the appearance of the skin, or even evolve into an overweight condition of the individual, possibly to the point of obesity.

Cellulite, considered to be unsightly, involves a hypertrophy of the adipose cells by overloading with triglycerides and a hyperviscosity of the ground substance (by polymerization of polysaccharides). These modifications impede exchanges between the cells and the mobility of the connective fibers (collagen, elastin and reticulin), which translates into water retention, slower venous and lymphatic circulation and loss of skin suppleness. The accentuation of the adipose tissue is localized, especially in women, in the area of the hips, thighs, buttocks, knees, and forearms. The skin takes on a quilted and padded appearance and in the most advanced stage an "orange peel" appearance, characterized by a succession of depressions caused by an excessive stretching of the connective segments and pulling of the epidermis toward the deep tissues.

At present, many research efforts have been carried out to find an effective way of fighting cellulite and excess fat in general. Many methods have been used, such as certain medical-surgical techniques like lipoplasty, lymph drainage, mesotherapy, ionophoresis techniques, etc. However, these techniques, while effective, are severe and restricting. Biological ways have been studied to act in a gentle and noninvasive manner on the mechanisms of formation of subcutaneous fat deposits.

Solutions have been proposed to intervene, in particular, in the metabolism of fatty acids. Cosmetic and pharmaceutical agents thus work on different levels to prevent the appearance of cellulite. For example, they will promote lipolysis, or rather inhibit lipogenesis, that is, reduce the formation of triglycerides.

The main objective of the present invention is to provide a new active ingredient for slimming. In fact, the inventors have succeeded in selecting particular substances having remarkable properties when applied to the skin.

Thus, by a first aspect, the object of the present invention is the use of an effective quantity of proteins of the SIRT family or peptide or polypeptide fragments of the SIRT family or biologically active derivatives of the latter, alone or in combination with at least one other active agent, to produce a localized slimming effect after being applied to the skin, and more particularly to reduce, eliminate or prevent fatty deposits under the skin.

According to one particularly advantage embodiment of the invention, the peptides belonging to the SIRT family are chosen among the peptides corresponding to the ID sequences N°:

(1)  Gly Ala Gly Ile Ser Thr (2)  Gly Ile Pro Asp Phe Arg Ser Pro (3)  Gly Ile Pro Asp Phe Arg (4)  Gly Ile Pro Asp Phe Arg Ser (5)  Gly Leu Tyr Asp Asn Leu Glu (6)  Thr Gln Asn Ile Asp Thr Leu

According to one especially preferred embodiment of the invention, the peptide fragment coming from the SIRT family has the ID sequence N° (5), that is, the sequence Gly Leu Tyr Asp Asn Leu Glu.

The invention also concerns the use of variant forms of these sequences and/or these fragments. The term "variant" denotes here a polypeptide or a peptide which differs, for example, from the sequence of a reference peptide while preserving its essential properties. Generally, the differences are limited such that the sequences of the reference peptide and those of the variant are quite similar and, in certain regions, identical.

Preferably, the variant forms are those which vary from the reference sequences by the substitution of chemically equivalent (or homologous) amino acids, that is, by the substitution of one residue for another one having the same characteristics. Thus, the classical substitutions are done between Ala, Val, Leu and Ile; between Ser and Thr; between the Asp and Glu acid residues; between Asp and Glu; between Asn and Gln; and between the basic residues Lys and Arg; or between the aromatic residues Phe and Tyr. The term variant also denotes a peptide that differs, for example, from the sequence of a reference peptide while preserving its essential properties. Generally, the differences are limited such that the sequences of the reference peptide and those of the variant are quite similar and, in certain regions, identical. A variant peptide and a reference peptide can thus differ from the sequence of amino acids by one or more substitutions, additions, deletions in all combinations.

The fragments of SIRT proteins of polypeptide or peptide kind that are described in the present invention also include the use of all biologically active fragments, or one of their analogues or variants. By the phrase biologically active is also meant fragments having an in-vivo or in-vitro activity characteristic of the activity of the compound according to the invention.

In the invention, the term "amino acid" refers here to any natural or nonnatural organic acid having the formula:

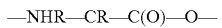
—NHR—CR—C(O)—O— where each —R is selected independently between a hydrogen and an alkyl group having between 1 and 12 carbon atoms. Preferably, at least one —R group of each amino acid is a hydrogen. By the term "alkyl" is meant here a carbon chain which can be linear or branched, substituted (mono- or poly-) or nonsubstituted; saturated, monosaturated (a double or triple bond in the chain) or polyunsaturated (two or more double bonds, two or more triple bonds, one or more double bonds and one or more triple bonds in the chain).

The term "peptide" denotes a chain of two or more amino acids joined together by peptide bonds or by modified peptide bonds; a polypeptide denotes a peptide of rather substantial size.

By peptide is meant the natural or synthetic peptide of the invention as described above or at least one of its fragments, whether obtained by proteolysis or synthetically, or any natural or synthetic peptide whose sequence is totally or partially made up of the previously described peptide sequence.

In order to improve the resistance to degradation, it may be necessary to use a protected form of the peptide per the invention. The form of protection should obviously be a biologically compatible form and it should be compatible with a use in the field of cosmetics or pharmaceuticals.

Many forms of biologically compatible protection can be contemplated, and are well known to the practitioner, such as for example acylation or acetylation of the amino-terminal end, or amidation or esterification of the carboxy-terminal end. Thus, the invention concerns a use such as was defined above, characterized in that the peptide is in a protected form or not. Preferably, one uses a protection based on the acylation or acetylation of the amino-terminal end, or the amidation or esterification of the carboxy-terminal end, or both of these forms. The amino acid derivatives and the peptide derivatives also include amino acids and peptides linked together by a pseudo-peptide bond. By "pseudo-peptide bond" is meant all types of bonds able to replace the "classical" peptide bonds.

In the field of amino acids, the geometry of the molecules is such that they can in theory be present in the form of different optical isomers.

In fact, there exists one molecular conformation of the amino acid (AA) which deviates to the right the plane of polarization of light (dextrorotatory or D-aa conformation), and one molecular conformation of the amino acid (aa) which deviates to the left the plane of polarization of light (levorotatory or L-aa conformation). Nature has chosen for natural amino acids only the levorotatory conformation. Consequently, a peptide of natural origin will consist only of amino acids of type L-aa. However, chemical synthesis in the laboratory lets one prepare amino acids having the two possible conformations. Thus, starting with this base material, it is possible to incorporate both amino acids in the form of dextrorotatory or levorotatory optical isomers during the peptide synthesis. And so the amino acids constituting the peptide according to the invention can be in the L and D configuration; preferably, the amino acids are in the L form. The peptides according to the invention can thus be in L, D, or DL form.

The peptides in the present patent can be obtained either by classical chemical synthesis (in solid phase or in homogeneous liquid phase), or by enzymatic synthesis (Kullman et al., J. Biol. Chem. 1980, 225, 8234) from component amino acids or their derivatives.

The peptides of the invention can likewise be obtained by fermentation of a strain of bacteria, whether modified or not, by genetic engineering to produce the peptides of the above indicated sequence and their fragments, or by extraction of proteins of animal or vegetable origin, preferably of vegetable origin, followed by a controlled hydrolysis which liberates the peptide fragments of medium size and of small size, according to the invention.

Very many proteins found in plants are likely to contain these sequences within their structure. Guided hydrolysis makes it possible to release these peptide fragments. It is possible, but not necessary to realize the invention, to either extract the particular proteins at first and then hydrolyze them, or to perform the hydrolysis at first for a crude extract and then purify the peptide fragments. It is also possible to use certain hydrolyzed extracts without purifying the peptide fragments of the invention, yet still making sure of the presence of said fragments by suitable analytical means.

Other more simple or more complex procedures can be contemplated by the practitioner who is familiar with the field of synthesis, extraction and purification of proteins and peptides. Thus, the peptides of the invention can be of natural or synthetic origin. Preferably, according to the invention, the peptides are obtained by chemical synthesis.

In the composition per the invention, the peptides can be a mixture of peptide derivatives and/or be made up of amino acid derivatives.

The peptides of the invention, of the composition containing them, have a very effective action on the adipocytes. In fact, they help significantly decrease the quantity of triglycerides contained in the adipocytes of the hypodermis.

This phenomenon is probably due to a blocking of the phenomenon of lipogenesis, that is, blocking of the process of storage of triglycerides resulting in a hypertrophy of the adipocytes. A control of lipogenesis, that is, the reaction of synthesis of triglycerides in the adipocytes, will help prevent a hypertrophy of the adipocytes, as well as a succeeding hyperplasia. Thus, when in the course of adipocyte differentiation the quantity of triglycerides present in the vacuoles does not increase, the volume of the adipocytes and their number also will not increase. The skin gradually returns to its "normal" appearance. The cellulite tissue develops no further, and the orange peel effect is diminished. The unattractive appearance of the body is softened little by little.

The peptides of the invention or the composition containing them thus makes it possible, primarily because of their particular and pronounced activity on adipogenesis, to prevent the appearance of cellulite, and fight its worsening. If cellulite has become established, the peptides per the invention or the composition containing them will improve the appearance of the skin and, for example, attenuate the "orange peel" appearance. All of these properties make them particularly useful in cosmetic and dermatological preparation for slimming purposes.

It is quite obvious that the invention is addressed to mammals in general and more particularly human beings.

According to a second aspect of the invention, the aforesaid peptides can be used in or for the making of a topical-use composition intended for the treatment of cellulite and/or treatment of orange-peel skin. The peptides or the composition containing them are advantageously used to reduce, eliminate, or prevent excess fatty deposits beneath the skin.

According to one advantageous embodiment of the invention, the aforesaid peptides are first solubilized in one or more cosmetically or pharmaceutically acceptable solvents that are classically used by the practitioner, such as water, ethanol, propylene glycol, butylene glycol, dipropylene glycol, ethoxylated or propoxylated diglycols, cyclical polyols, vaseline, glycerol (glycerine, a vegetable oil, or any mixture of these solvents.

According to another advantageous embodiment of the invention, the aforesaid peptides are first solubilized in a cosmetic or pharmaceutical vector such as liposomes or adsorbed onto powderlike organic polymers, mineral supports such as talc and bentonite, and more generally solubilized in, or fixed to, any cosmetically or pharmaceutically acceptable vector.

The effective quantity of active ingredient corresponds to the quantity needed to obtain the desired result.

According to one advantageous embodiment of the invention, the aforesaid peptides are present, in the compositions of the invention, in a concentration between around 0.005 and 500 ppm (parts per million), and preferably in a concentration between around 0.1 and 50 ppm in weight as compared to the total weight of the final composition.

The composition containing the peptides per the invention can be a cosmetic or dermatological or pharmaceutical composition. Preferably, according to the invention, the composition is a cosmetic composition, since it is intended to improve the appearance and general performance of the skin of the person who uses it.

The composition per the invention is preferably a cosmetic and/or dermatological composition adapted for administration by topical skin route, containing a cosmetically or pharmaceutically acceptable medium.

These compositions could, in particular, be present in the form of an aqueous, water-alcohol, or oily solution, water-in-oil, or multiple emulsions; they can also be present in the form of suspensions, or powders, adapted to an application on the skin, the mucous membranes, the lips and/or the hair.

These compositions can be more or less fluid and have the appearance of a cream, a lotion, a serum, a pomade, a gel, a paste or a foam. They can also be present in solid form, such as a stick, or be applied to the skin in the form of an aerosol.

These compositions, moreover, contain any additive customarily used in the contemplated area of application, as well as the adjuvants needed for their formulation, such as solvents, thickeners, silicones, diluents, antioxidants, colorants, sun screens, self-tanning agents, pigments, ballasts, preservatives, perfumes, deodorants, cosmetic or pharmaceutical active agents, essential oils, vitamins, essential fatty acids, surfactants, film-forming polymers, etc.

For example, in said compositions the peptides per the invention can advantageously be combined with any other ingredient stimulating the exfoliation of the skin, inhibiting lipogenesis or stimulating lipolysis, such as derivatives of xanthine. One can mention, for example, caffeine, theophyllin, theobromin, acephyllin, nicotinate of xanthinol, diniprophyllin, diprophyllin, etamiphyllin and its derivatives, etophyllin, proxyphyllin, pentophyllin, propentophyllin, pyridophyllin and bamiphyllin.

In all these cases, the practitioner will make sure that these adjuvants, active or inactive, as well as their proportions are chosen in such a way as not to harm the advantageous properties sought from the composition per the invention. These adjuvants may, for example, correspond to 0.01 to 20% of the total weight of the composition.

If the composition of the invention is an emulsion, the fatty phase can represent from 5 to 80% by weight and preferably 5 to 50% by weight as compared to the total weight of the composition. The emulsifiers and coemulsifiers used in the composition will be chosen among those classically used in the field in question. For example, they can be used in a proportion ranging from 0.3 to 30% by weight, in relation to the total weight of the composition.

According to a third aspect of the invention, the aforesaid peptides can be used in or to make a pharmaceutical composition for topical use, intended for the treatment of cellulite and/or for the treatment of excess fat deposits beneath the skin.

According to a fourth aspect, the present invention concerns a method of cosmetic care to achieve a slimming effect. As well as a method of cosmetic care intended to reduce, eliminate and/or prevent excess fat deposits beneath the skin, and/or intended to fight cellulite and/or fight the orange-peel skin effect, consisting in applying, topically, to the zones of skin affected, an effective quantity of at least one of the aforesaid peptides.

The method of slimming cosmetic care also concerns the regular application of composition per the invention topically to the zones of the face or body being slimmed down, in particular the hips, the buttocks, the thighs, the stomach, the face.

The advantage of the present invention is that it can provide an effective topical treatment for adiposity while making use of "gentle" methods.

Other advantages and characteristics of the invention will appear better from a reading of the examples, given by way of illustration and not limitation.

EXAMPLE 1

Demonstration of the Activity of the Peptides of the Invention on the Adipocytes 1) Principle of the In-Vitro Test Demonstration of the biological activity of the peptides per the invention was done with the pre-adipocyte cell line 3T3-L1, subjected to a differentiation into mature adipocytes. The number and the size of the lipid vacuoles present in the mature adipocytes are evaluated by microscope observation after specific staining with the "Oil Red" stain.

2) Experimental Protocol

The pre-adipocyte cells 3T3-L1 are seeded in Labteks and maintained until 100% confluence in DMEM 10% SVF culture medium. The cells are treated with the peptide of sequence ID N° (5), representative of the family of peptides per the invention, placed in 1% solution à 1% starting with a solution of 50 ppm. Nontreated controls were prepared in parallel.

Once confluence is achieved, the cells are cultivated in the presence of differentiation inducers (IBMX, dexamethasone and insulin), so as to bring about the final differentiation into mature adipocytes. The differentiated adipocytes are further incubated for 3 hours with the peptide being tested in a concentration of 1%. Nontreated controls were prepared in parallel.

The adipocytes are then fixed for 10 minutes in a 4% formol and NaCl solution, after which the "Oil Red" stain solution (Sigma, 0-0625) is applied for 15 minutes. The cells are then rinsed with warm water and mounted on slides, in hydrophilic medium (Aquatex). The observation is done under an optical microscope.

3) Results

The results of the observation of the cells show that the mature adipocytes of the nontreated controls have a voluminous spherical shape and show a major accumulation of intra-cytoplasmic lipid vesicles; on the other hand, the mature adipocytes treated by a solution containing the peptide of the invention have a less rounded morphology and a clearly diminished content of intra-adipocyte lipid vesicles.

|  | Control | Peptide of sequence ID N° (5) |
|---|---|---|
| Size/number of lipid droplets | ++++ | ++ |

4) Conclusions

The solution containing the peptide of the invention proves to be particularly effective in the process of limitation of adipocyte hypertrophy. Thus, it allows for an elimination of the triglycerides contained in the intra-adipocyte vesicles.

EXAMPLE 2

Preparation of Compositions

1—Slimming Cream

| Commercial names | INCI Names | % by mass |
|---|---|---|
| PHASE A | | |
| Montanov 68 | Cetearyl Alcohol (and) Cetearyl Glucoside | 5.00 |
| Squalane | Squalane | 2.50 |
| DUB IPP | Isopropyl Palmitate | 3.50 |
| Eutanol G | Octyldodecanol | 1.50 |
| Phenonip | Phenoxyethanol (and) Methylparaben (and) Ethylparaben (and) Butylparaben (and) Propylparaben (and) Isobutylparaben | 0.50 |
| PHASE B | | |
| Demineralized water | Aqua (Water) | Qsp |
| Glycerine | Glycerin | 3.00 |
| Butylene Glycol | Butylene glycol | 3.00 |
| PHASE C | | |
| Simulgel EG | Sodium Acrylate/Acryloyldimethyl Taurate Copolymer (and) Isohexadecane (and) Polysorbate 80 | 0.60 |
| PHASE D | | |
| Peptide per the invention | | 1.25 ppm |
| Perfume | Perfume (Fragrance) | Qsp |
| Colorant | | Qsp |

Operating Procedure

The constituents of phase A are melted at 75° C. and the constituents of phase B heated to 75° C. Phase A is emulsified in B, then the mixture is cooled below 40° C. Phases C and D are then added under constant agitation.

2—Firming-Slimming Spray

| Commercial names | INCI Names | % by mass |
|---|---|---|
| PHASE A | | |
| Emulgade SEV | Glyceryl Stearate (and) Ceteareth-20 (and) Ceteareth-12 (and) Cetearyl Alcohol | 4.60 |
| Eumulgin B2 | Ceteareth-20 | 1.40 |
| Cetiol OE | Dicaprylyl Ether | 3.00 |
| DUB B1215 | C12-C15 Alkyl Benzoate | 5.00 |
| Phenonip | Phenoxyethanol (and) Methylparaben (and) Ethylparaben (and) Butylparaben (and) Propylparaben (and) Isobutylparaben | 0.50 |
| DUB ININ | Isononyl Isononanoate | 5.00 |
| PHASE B | | |
| Demineralized water | Aqua (Water) | 15.00 |
| Glycerine | Glycerin | 3.00 |
| PHASE C | | |
| Demineralized water | Aqua (Water) | Qsp |
| PHASE D | | |
| Peptide per the invention | | 1.50 ppm |
| Perfume | Perfume (Fragrance) | qsp |
| Colorant | | qsp |

Operating Mode

The constituents of phase A and phase B are heated separately to 65° C.; phase B is incorporated in phase A under agitation. The temperature of the mixture is increased to 83° C., then it is cooled to the phase inversion temperature. Phase C is then added. The active ingredient is incorporated when the temperature reaches less than 40° C. It is then possible to add fragrances and/or colorants.

3—Firming-Slimming-Anti-Cellulite Gel

| Commercial names | INCI Names | % by mass |
|---|---|---|
| 1. Carbopol Ultrez 10 (2%) | Carbomer | 25.00 |
| 2. Demineralized water | Aqua (Water) | Qsp |
| 3. DUB DIOL | Methyl Propanediol | 3.00 |
| 4. EDTA | Tetrasodium EDTA | 0.10 |
| 5. Glydant Plus Liquid | DMDM Hydantoïn (and) Iodopropynyl butylcarbamate | 0.20 |
| 6. Peptide per the invention | | 1.25 ppm |
| 7. TEA | Triethanolamine | 0.50 |
| 8. Perfume | Perfume (Fragrance) | Qsp |
| 9. Water-soluble colorant | | Qsp |

Operating Mode

The Carbopol gel is prepared at 2%. The ingredients are added in the order enumerated above, under agitation. The mixture is then neutralized with the TEA. The fragrance and colorants are added if necessary.

The invention claimed is:

1. A cosmetic, pharmaceutical and/or dermatological composition for reducing excess fat deposits beneath the skin, and/or treating cellulite and/or treating the orange-peel skin effect, comprising:
at least one isolated peptide from the sirtuins (SIRT) family as an active sliming agent, alone or in combination with at least one other active agent; and a cosmetic, pharmaceutical and/or dermatological acceptable medium, wherein said at least one isolated peptide is Gly Leu Tyr Asp Asn Leu Glu (SEQ ID NO: 5), and wherein said at least one isolated peptide has at least one functional group protected by a protecting group formed by an acylation or an acetylation of the amino-terminal end, or an amidation or an esterification of the carboxy-terminal end, or both.

2. The composition according to claim 1, further comprising a cosmetically acceptable lipolytic agent.

3. The composition according to claim 2, wherein the lipolytic agent is selected from the group consisting of caffeine, acephyllin, nicotinate of xanthinol, diniprophyllin, diprophyllin, etamiphyllin, etophyllin, proxyphyllin, pentophyllin, propentophyllin, pyridophyllin, bamiphyllin, theophylline, and theobromin.

4. The composition according to claim 1, wherein the at least one isolated peptide is present in the composition in a concentration between around 0.005 and 500 ppm.

5. The composition according to claim 1, wherein the at least one isolated peptide is first solubilized in one or more cosmetically or pharmaceutically acceptable solvent selected from the group consisting of water, ethanol, propylene glycol, glycerol, butylene glycol, dipropylene glycol, ethoxylated or propoxylated diglycols, cyclical polyols, vaseline, a vegetable oil, and mixtures thereof.

6. The composition according to claim 1, wherein the at least one isolated peptide is first solubilized in a cosmetic or pharmaceutical vector or a mineral support.

7. The composition according to claim 1, wherein the at least one isolated peptide is fixed to a cosmetically or pharmaceutically acceptable vector.

8. The composition according to claim 1, wherein the at least one isolated peptide is in a galenical form adapted for application on the skin, the mucous membranes, the lips and/or the hair selected from the group consisting of aqueous solutions, water-alcohol solutions, oily solutions, oil-in-water emulsions, water-in-oil emulsions, or multiple emulsions, suspensions, shampoos, sticks, sprays and powders.

9. A cosmetic, pharmaceutical and/or dermatological composition for reducing fat deposits beneath the skin, and/or treating cellulite and/or treating the orange-peel skin effect, comprising:
at least one isolated peptide from the SIRT family as an active slimming agent, alone or in combination with at least one other active agent;
a cosmetic, pharmaceutical and/or dermatological acceptable medium; and
a cosmetically acceptable lipolytic agent, wherein said at least one isolated peptide is Gly Leu Tyr Asp Asn Leu Glu (SEQ ID NO: 5).

10. The composition according to claim 9, wherein the lipolytic agent is selected from the group consisting of caffeine, acephyllin, nicotinate of xanthinol, diniprophyllin, diprophyllin, etamiphyllin, etophyllin, proxyphyllin, pentophyllin, propentophyllin, pyridophyllin, bamiphyllin, theophylline, and theobromin.

11. The composition according to claim 9, wherein the at least one isolated peptide has at least one functional group protected by a protecting group formed by an acylation or an acetylation of the amino-terminal end, or an amidation or an esterification of the carboxy-terminal end, or both.

12. The composition according to claim 9, wherein the at least one isolated peptide is present in the composition in a concentration between around 0.005 and 500 ppm.

13. The composition according to claim 9, wherein the at least one isolated peptide is first solubilized in one or more cosmetically or pharmaceutically acceptable solvent selected from the group consisting of water, ethanol, propylene glycol, glycerol, butylene glycol, dipropylene glycol, ethoxylated or propoxylated diglycols, cyclical polyols, vaseline, a vegetable oil, and mixtures thereof.

14. The composition according to claim 9, wherein the at least one isolated peptide is first solubilized in a cosmetic or pharmaceutical vector or a mineral support.

15. The composition according to claim 9, wherein the at least one isolated peptide is fixed to a cosmetically or pharmaceutically acceptable vector.

16. The composition according to claim 9, wherein the at least one isolated peptide is in a galenical form adapted for application on the skin, the mucous membranes, the lips and/or the hair selected from the group consisting of aqueous solutions, water-alcohol solutions, oily solutions, oil-in-water emulsions, water-in-oil emulsions, or multiple emulsions, suspensions, shampoos, sticks, sprays and powders.

\* \* \* \* \*